United States Patent
Lee et al.

(10) Patent No.: US 11,488,712 B2
(45) Date of Patent: Nov. 1, 2022

(54) DIAGNOSTIC EFFECTIVENESS TOOL

(71) Applicant: Google LLC, Mountain View, CA (US)

(72) Inventors: Ryan Lee, Mountain View, CA (US);
Andrej Cedilnik, Sunnyvale, CA (US);
Christopher So, Mountain View, CA (US);
Fabian Schlup, Mountain View, CA (US);
Robertus Christianus Elisabeth Mariet, Mountain View, CA (US);
Minal Mehta, Mountain View, CA (US);
Eleonora Merjanova Mihov, Mountain View, CA (US)

(73) Assignee: Google LLC, Mountain View, CA (US)

( * ) Notice: Subject to any disclaimer, the term of this patent is extended or adjusted under 35 U.S.C. 154(b) by 1326 days.

(21) Appl. No.: 15/692,550

(22) Filed: Aug. 31, 2017

(65) Prior Publication Data
US 2019/0065688 A1 Feb. 28, 2019

(51) Int. Cl.
*G16H 50/20* (2018.01)
*G16H 10/60* (2018.01)
(Continued)

(52) U.S. Cl.
CPC .............. *G16H 50/20* (2018.01); *G06N 5/04* (2013.01); *G06N 7/005* (2013.01); *G06Q 10/10* (2013.01);
(Continued)

(58) Field of Classification Search
CPC ......... G16H 50/20; G16H 50/70; G16H 10/60
See application file for complete search history.

(56) References Cited

U.S. PATENT DOCUMENTS 6,450,956 B1 9/2002 Rappaport et al.
6,678,669 B2 1/2004 Laipointe et al.
(Continued)

FOREIGN PATENT DOCUMENTS

CN 101169863 A 4/2008
CN 105190634 A 12/2015
(Continued)

OTHER PUBLICATIONS

Watkins, David et al., "A Cost-Effectiveness Tool to Guide the Prioritization of Interventions for Rheumatic Fever and Rheumatic Heart Disease Control in African Nations", PLOS Neglected Tropical Diseases, Aug. 11, 2016, pp. 1-15.
(Continued)

*Primary Examiner* — Jonathan Durant
(74) *Attorney, Agent, or Firm* — McDonnell Boehnen Hulbert & Berghoff LLP

(57) ABSTRACT

A system is disclosed for evaluating diagnostic effectiveness of one or more diagnostic tests or additional findings from a set of known findings as to a patient. The system includes a computing device containing a software application which is used by a healthcare provider to review the patient's medical history and enter findings as to the patient's condition or symptoms, a system storing a validated probabilistic health model including a database of medical knowledge informed from aggregated electronic medical records or other sources of medical knowledge; and a medical knowledge-based inference engine operating on the patient's medical history and findings and the validated probabilistic health model. The engine determines a set of the most probable diseases of the patient, suggests a set of one or more tests or additional findings that differentiate the set of most probable diseases, and generates indicia indi-
(Continued)

cating diagnostic effectiveness or relevancy of the one or more tests or additional findings.

24 Claims, 10 Drawing Sheets

(51) Int. Cl.
    *G06N 7/00*     (2006.01)
    *G06N 5/04*     (2006.01)
    *G16H 50/70*     (2018.01)
    *G06Q 50/22*     (2018.01)
    *G16H 70/20*     (2018.01)
    *G06Q 10/10*     (2012.01)

(52) U.S. Cl.
    CPC .......... *G06Q 50/22* (2013.01); *G16H 10/60* (2018.01); *G16H 50/70* (2018.01); *G16H 70/20* (2018.01)

(56) References Cited

U.S. PATENT DOCUMENTS

| | | |
|---|---|---|
| 6,988,088 B1 | 1/2006 | Miikkulainen et al. |
| 7,593,913 B2 | 9/2009 | Wang et al. |
| 8,315,883 B2 | 11/2012 | Sakurai |
| 8,521,556 B2 | 8/2013 | Chbat et al. |
| 8,645,165 B2 | 2/2014 | Belcher et al. |
| 2010/0174555 A1* | 7/2010 | Abraham-Fuchs .... G16H 20/30 706/46 |
| 2012/0290310 A1* | 11/2012 | Watson ................. G16H 10/60 706/50 |
| 2013/0268203 A1* | 10/2013 | Pyloth ................... G16H 50/20 702/19 |
| 2014/0108040 A1 | 4/2014 | Belcher et al. |
| 2014/0358570 A1* | 12/2014 | Tesanovic ............. G16H 50/70 705/2 |
| 2015/0019241 A1 | 1/2015 | Bennett et al. |
| 2016/0004829 A1* | 1/2016 | Beqaj .................... G06Q 10/10 705/2 |
| 2017/0024521 A1* | 1/2017 | Nakamura ............. G16H 50/20 |
| 2017/0199987 A1* | 7/2017 | Loeb ..................... G16H 50/70 |
| 2018/0011980 A1* | 1/2018 | Contu ................... G16H 50/30 |

FOREIGN PATENT DOCUMENTS

| | | | |
|---|---|---|---|
| CN | 106778039 A | 5/2017 | |
| WO | WO-2016097886 A1 * | 6/2016 | ............ G16H 50/20 |

OTHER PUBLICATIONS

Spector, "Utilization Review and Managed Health Care Liability," South Med. Journal, 2004 vol. 97 No. 3.

\* cited by examiner

Fig. 2

PERTINENT FINDINGS
- Sharp abdominal pain
- Fever
- Myalgia
- No jaundice
- No cough
- Add finding

200

| Scleral icterus | Dark urine | Skin Erythema | Test 1 | Test 2 |

202  204

ASSESSMENT & PLAN

| Poss. uncomplicated malaria 2 2 1 | Fever treatment 2 1 | Dehydration 1 1 |

✗ DISCARD    SAVE DRAFT    SUBMIT ▶

40
12

DIAGNOSTIC EFFECTIVENESS TOOL

BACKGROUND

This disclosure is directed to systems and methods for improving the efficiency and effectiveness of diagnostic and treatment decision making.

The diagnostic process begins when a patient arrives with a chief complaint. Before seeing the patient, the physician first searches through the patient's medical record for pertinent findings in the patient's history. From these findings, he creates a differential diagnosis, a broad list of diagnoses that is ranked based on the prevalence of each disease. The decision to test for a finding (ask a question, do an examination procedure, order a diagnostic test, etc.) is based on things such as:

- the finding's effectiveness in differentiating between top ranked diagnoses (depends on the finding's positive and negative likelihood ratios (LR) for each disease);
- the finding's ability to rule out emergent diseases (e.g., while rare, myocardial infarction should be ruled out with an ECG in patients with chest pain); and
- the cost to obtain the finding (iatrogenic risk, resource availability, timeliness, etc.).

The physician interprets every newly acquired finding in the context of the patient's history, which changes the probability of each possible diagnosis. This process occurs after every clinical decision. Once there are enough findings to support a definitive diagnosis (high probability diagnosis with low probability alternatives), a diagnosis is made and treatment begins.

The above process can be inefficient and not cost-effective, for a variety of reasons. For one thing, a physician may not have time to search through the medical record for all relevant findings in the patient's history, particularly where the patient has an extensive or complex medical history. Furthermore, it may be difficult for the physician to objectively interpret the relevance of a finding for every diagnosis. It is difficult to rapidly make cost-effective, evidence-based decisions, especially where the patient has a complex medical history or information on costs of different potential tests are not readily available. Furthermore, often physicians do not have time to document a high-quality note about the diagnostic process that occurred, especially in a busy clinical practice or hospital situation.

Physicians and insurance companies struggle to find a balance between high quality healthcare and economical use of resources when delivering care to patients. Providers and payers often disagree about a patient's care because physicians are ill informed about the market, costs, and availability of resources, while payers lack the physician's experience and details about the patient's presentation. Communication is a slow and complex process, usually requiring a doctor to request authorization for a test from the patient's insurance company. This system creates an adversarial relationship between providers and payers, while excluding patients from the discussion entirely.

It is believed that no single technology adequately addresses all the above problems. Decision-making models (using Bayes' theorem) are used in clinical medicine, but in practice, they only serve as a mental framework for objectivity. Where there is objective data, the decision to order a test for a patient can be supported by test's sensitivity and specificity, as long as the patient falls in the population that was studied in the clinical trial. Health insurance companies have an adjudication process for authorizing reimbursement. They determine whether a study ordered by a physician is justified by its cost. Decisions are based on static rules or guidelines created by a committee.

Coded vocabularies are used for storing, retrieving, researching, and sharing patient data (i.e. HL7/FHIR, ICD, UMLS, SNOMED, and many others). Some databases have used these vocabularies to describe relationships between symptoms and diseases (Disease Database), which power online triage and symptom checkers. Symcat and Isabel Healthcare use probabilistic models to determine what question to ask next, but the critical components for clinical decision-making (physical exam findings, lab values, imaging reports, etc.) are excluded, making these tools not useful outside of patient education.

Clinical decision support (CDS) systems is a broad category of simple tools available to physicians, usually integrated with the EMR. Some of these tools use information from the patient's medical record. Some examples include:

- Cancer screening reminders: The physician's dashboard has a list of patients due for screening, based on age and gender.
- Alerts for possible drug interactions: e.g., an alert appears when the physician orders a quinolone for a patient on warfarin.
- Clinical pathways: A guideline for asthma management appears in the chart of a patient who has a history of asthma.

CDS tools are usually implemented as point-fixes for specific metrics, like compliance rates or number of near-miss events. Therefore, they appear like regulatory tasks because they are not integrated with the physician's workflow/the diagnostic process. While CDS tools may improve metrics, their effectiveness is limited because they simply enforce rules based on static evidence.

Medication reconciliation is a process for creating and maintaining an accurate list of medications by comparing what the patient reports to be taking with what the physician has ordered. Medication reconciliation is integrated in most electronic medical records (EMRs). The technology is limited to medications, it is not predictive, and it is not integrated with the diagnostic process.

Assistance with documentation is available in the form of software, tools, and personnel. EMRs use macros to expand text for frequently typed phrases or paragraphs. Forms can also be inserted to free text notes or customized into templates. Canvas Medical has tools like word-autocompletion and keyword-to-ICD10 conversion. Documentation tools have been criticized for perpetuating "note bloat". These tools are meant to improve the quality and efficiency of documentation, but bury the pertinent data instead. While efforts have been made to extract pertinent findings from free text, the results have been variable and are not in widespread use today.

SUMMARY

A system and method is disclosed for evaluating, in advance, the medical effectiveness of diagnostic tests, new findings or interventions (i.e., treatments) from a set of known findings as to a patient and presenting the results to healthcare providers, healthcare payers (e.g., insurance companies), and/or patients. This disclosure is also directed to component aspects and combinations of the system.

In one embodiment the system generates data for a computing device containing a software application which is used by a healthcare provider to assist in reviewing the patient's medical history and entering new findings as to the patient's condition or symptoms.

The system includes a validated probabilistic model that is informed from aggregated electronic medical records and other sources of medical knowledge, such as medical journal articles, or expert user input. The system further includes a medical knowledge-based inference engine (processing unit and associated programming) that uses the patient's known findings (i.e., medical history and new findings, if any) and the model to determine a set of the most probable diseases. The engine also suggests a set of one or more tests or new findings that, it present, differentiate the set of most probable diseases, and generates indicia (e.g., text, scores, probability or statistical data, etc.) indicating diagnostic effectiveness of the one or more findings or tests, e.g., using Bayesian inference.

This set of one or more tests or findings and associated indicia that are suggested by the engine can be transmitted to the computing device and presented to a user, e.g., healthcare provider, patient or payer. These results and indicia could be presented on the computing device for aiding the healthcare provider in selecting additional tests or findings to pursue. Alternatively the results could be presented on a payer interface, e.g., a computer or workstation used by payer. The payer can make reimbursement (e.g., coverage and/or authorization) decisions based on the indicia.

BRIEF DESCRIPTION OF THE DRAWINGS

FIG. 2 is an illustration of a health-care provider facing interface of an electronic device (workstation, tablet computer, smartphone, etc.) showing a display of current findings, and suggested additional findings or tests for the provider to make to work towards a diagnosis.

DETAILED DESCRIPTION

Figure 1:
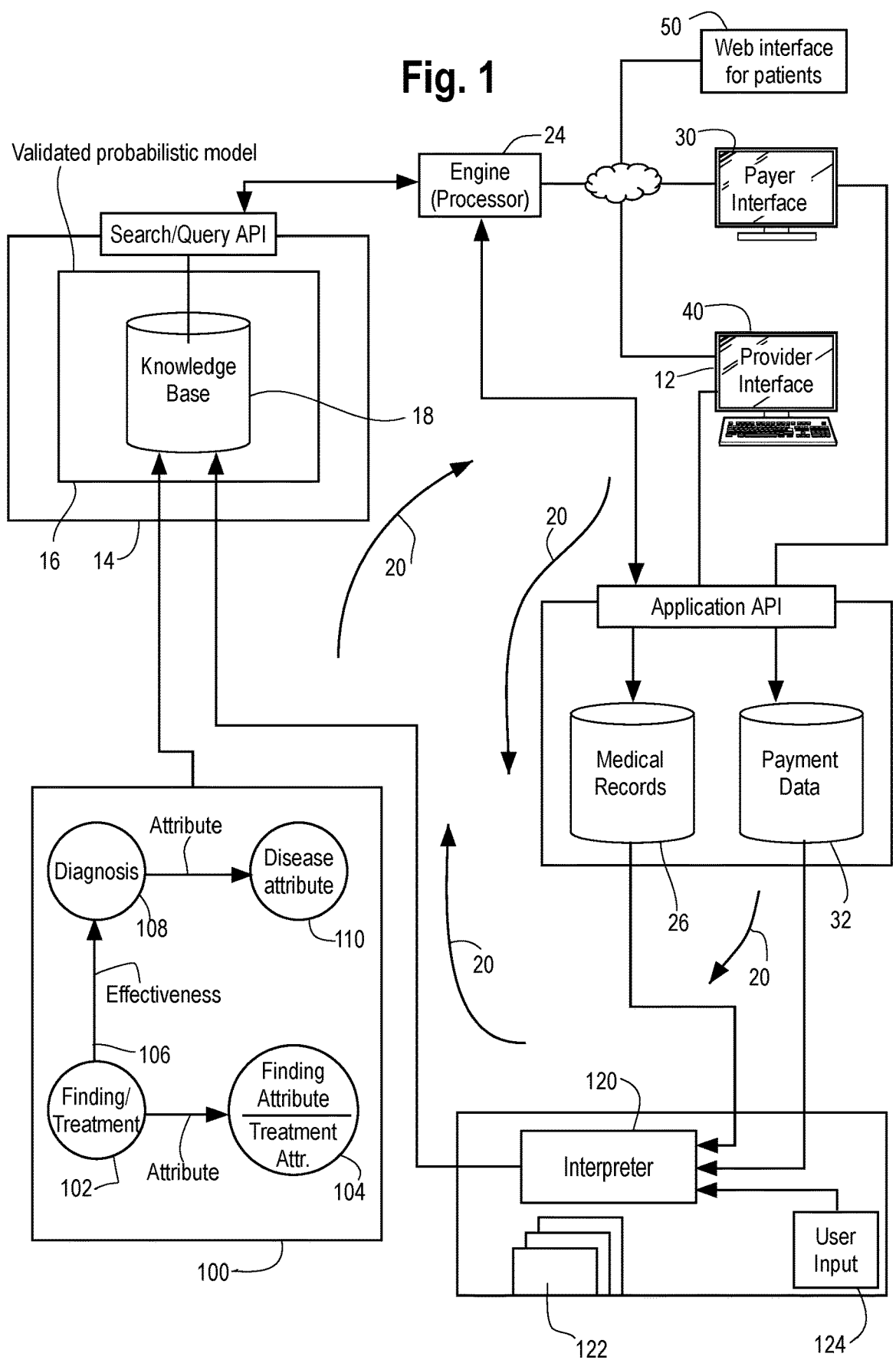
FIG. 1 is a block diagram of a system which includes features of the present disclosure.

FIG. 1 is directed to a system 10 for evaluating diagnostic effectiveness of one or more tests or additional findings from a set of known findings as to a patient. In the illustrated embodiment the system is part of or embedded in a larger clinical decision making system including device and software components aiding healthcare providers in arriving at a diagnosis and treatment options for a patient.

The system generates data for a computing device 12 (which may take the form of a tablet, smartphone or desktop computer or workstation) containing a software application which is used by a healthcare provider to review the patient's medical history and enter findings as to the patient's condition or symptoms. This device 12 and the application will be described in more detail in FIGS. 2-8 and the discussion which follows.

A system 14, which may be configured as a computer or complex of computers with ancillary memory, stores a validated probabilistic health model 16 and a database 18 of medical knowledge informed from aggregated electronic medical records or other sources of medical knowledge. The aggregated electronic medical records could come from an institution or multiple institutions, as well as electronic medical records fed back into the system by means of the flow of data indicated by the arrows 20. In a situation where the knowledge base is based on aggregated health records, data is patient de-identified such that compliance with all requirements for disclosure and use of a limited data set under HIPAA is performed. Ethics review and institutional review board exemption is obtained from each institution as necessary. Patient data is not linked to any Google user data. Furthermore, aggregated electronic health records are stored in a sandboxing infrastructure that keeps each EHR dataset separated from each other, in accordance with regulation, data license and/or data use agreements. The data in each sandbox is encrypted; all data access is controlled on an individual level, logged, and audited.

The validated probabilistic health model and medical knowledge base includes a search and query application programming interface (API) 22 as will be explained below.

The system 10 also includes a medical knowledge-based inference engine 24 (processor and associated programming), which operates on the patient's medical history and findings (either provided directly by the device or from a medical records database 26) and the validated probabilistic health model 16. The engine is programmed to performs several tasks, including (1) determine a set of the most probable diseases of the patient, (2) suggest a set of one or more tests or additional findings that differentiate the set of most probable diseases, and (3) generate indicia, such as statistical data, text, or otherwise, indicating the effectiveness or relevancy of the one or more tests or additional findings. These aspects will be described in greater detail below. Data reflecting the results of these tasks are transmitted from the engine to the electronic device 12 to assist the healthcare provider in managing and planning the patient's care more efficiently.

For example, the electronic device 12 includes an interface 40 for presenting to the healthcare provider information as to at least one of (i) the set of the most probable diseases of the patient, (ii) a set of one or more tests or additional findings that differentiate the set of most probable diseases, (iii) the indicia indicating effectiveness or relevancy of the one or more tests or additional findings, or (iv) visualizations of the suggestions made by the inference engine. In one embodiment, some or all of the above are displayed on the interface, e.g., in a series of screen displays with suitable controls or tools for toggling between the various features which are displayed. Examples will be described below.

In one embodiment, there is a computer workstation 30 residing on a payer network (not shown) which includes an application receiving the data from the engine as to the proposed additional findings or tests and the indicia, e.g. cost and relevancy scores. The application is configured to facilitate reimbursement or authorization decisions regarding the one or more tests. For example, an employee of the payer at the workstation views the proposed additional test(s) and associated indicia, and consults cost data either residing on the payer network, included in the indicia, or obtained from a database 32, and makes reimbursement or coverage decisions on the proposed additional test(s).

Additionally, the system further supports a web-based patient interface 50 providing patients with diagnostic effectiveness information which they can access from their own electronic device, such as smartphone or PC. As with the case of the provider device 12, the interface provides a display of at least one of (i) the set of the most probable diseases of the patient and (ii) a set of one or more tests or additional findings that differentiate the set of most probable diseases, (iii) the indicia indicating effectiveness or relevancy of the one or more tests, or (iv) visualizations of the suggestions made by the inference engine. These features allow the patient to make informed decisions about proposed tests which the provider may be recommending.

As noted above, in order for the inference engine to perform its tasks, including determine a set of the most probable diseases of the patient, suggest a set of one or more tests or additional findings that differentiate the set of most probable diseases, and generate indicia, such as statistical data, text, or otherwise, indicating the effectiveness or relevancy of the one or more tests or additional findings, it uses the knowledge base 18 and the validated probabilistic health model 16. The knowledge base 18 includes validated (i.e., proven or established) medical knowledge in the form of data indicating relationships between medical findings (i.e., facts as to a patient condition, such as test results, symptoms, etc.) and diagnoses. The medical knowledge may be stored in a data structure format which preserves these relationships as indicated in the box 100. In particular, a finding, or a treatment, has one or more attributes 104. For example, a finding attribute such as "abdominal pain" may have an attribute of "cost" of zero, since the finding can be made by interview of the patient and no expensive test is needed. A finding such as "loss of bone mineral density" may have an attribute of $2,000, as in order to make such a finding a DEXA (dual energy X-ray absorptiometry) scan is required which has, say, an average cost of $2,000.

The medical knowledge includes an effectiveness relationship (106) between the finding 102 and a diagnosis 108. For example, a finding of abdominal pain has a sensitivity of 0.7 and a specificity 0.6 towards a diagnosis of "gastroenteritis." The diagnosis 108 has attributes 110, which may for example be severity, frequency (i.e., how common or rare the disease in a given population), or relationships to other diseases. For example the "gastroenteritis" diagnosis has a severity=2 on a scale of 1-10.

The system of FIG. 1 is preferably configured to augment or increase the knowledge base 18 over time as more and more patients are treated by the system of FIG. 1. In this regard, there is a computer 120 functioning as an interpreter which looks at raw information and turns it into a format useful to the knowledge base. The interpreter generates useful data and updates which can be applied to the knowledge base 18. For example, the interpreter accesses document sources 112, for example scientific papers, journals, clinical guidelines, Centers for Disease Control bulletins, etc. and formats the validated knowledge or information contained therein into the format consistent with the format 100 described above and supplies the additional medical knowledge to the knowledge base 18. In particular, the interpreter 120 constructs relationships between medical findings and diagnoses, effectiveness scores for the relationships, and attributes of the findings and the diagnoses. This can be done manually (by experts reviewing de-identified patient health records, medical journals, etc.) or using machine-learning models. Additionally, as indicated by the expert user input 124, qualified trained medical personnel may be provided with simple tools to construct relationships between findings and diagnoses, and assign attributes to findings and diagnoses, and such data is formatted by the interpreter 120 and supplied to the knowledge base 18. Additionally, application data, e.g., medical records 26 and payment data 32 may be provided to the interpreter 120 and added to the knowledge base, e.g., as attributes of findings or diagnoses or new relationships and attributes of findings and diagnoses. In essence, the flow of data through the system indicated by the arrows 20 improves the knowledge base 18 and the performance of the engine 24 over time in recommending additional findings, additional tests, suggested diagnoses, and generation of useful and accurate indicia accompanying the proposed additional tests or findings.

User Interface 40 of Electronic Device 10 (FIG. 2)

With the above description in mind, attention is directed to FIG. 2 which is an illustration of the provider interface 40 of an electronic device 12 of FIG. 1, for example a tablet computer. The interface 40 is designed to assists physicians through the diagnostic process and documents the process as it occurs, and provide a tool for evaluating medical effectiveness of proposed additional findings or tests. The interface 40 allows the physician to review a patient's medical history and enter new findings through assistance powered by a medical knowledge-base 18 and the inference engine 24.

The interface 40 has a region for display of three types of information that a physician can collect about a patient: 1) known findings, shown in region 200, 2) proposed new findings in region 202, including proposed new tests 204, and 3) a differential diagnosis, not shown in FIG. 2 but available through appropriate menu selection and shown in FIGS. 3, 4, 5 and 6. In the known findings section 200, the system suggests relevant facts from the patient's history that the physician confirms or denies with one tap. In the new findings section 202, the system suggests findings that are unknown and can be confirmed or denied by the physician (through questioning, examining, or placing an order and getting a result). In the differential diagnosis section, the system shows a differential diagnosis with the given known and new findings, ranked by probability. See FIGS. 3, 4, 5, and 6.

After confirming or denying a finding in region 200 or 202, the differential diagnosis is refreshed. Suggestions may change depending on the probabilities of diagnoses in the differential. The physician may continue to confirm/deny findings, or manually add new findings to arrive closer to a definitive diagnosis.

For example, a physician sees a patient with a chief complaint of "breast lump". He would see relevant findings 202 that have been previously recorded, such as "family history of breast cancer". The physician can confirm this finding and document it with one tap. This would increase the likelihood of breast cancer, ranking it higher in the differential diagnosis. In the new findings section 202, the physician sees suggested facts to confirm or deny: "recurrent" and "immobile". He asks the patient if her lump is recurrent, which she denies. He then performs a physical exam and finds an that the mass is immobile. Both findings are documented with a single tap, which increases the likelihood of breast cancer, putting it at the top in the differential diagnosis section. Next, the system suggests "diagnostic mammogram" in the new findings section devoted to proposed new tests, region 204 in FIG. 2. Tapping it places the order.

Figure 3:
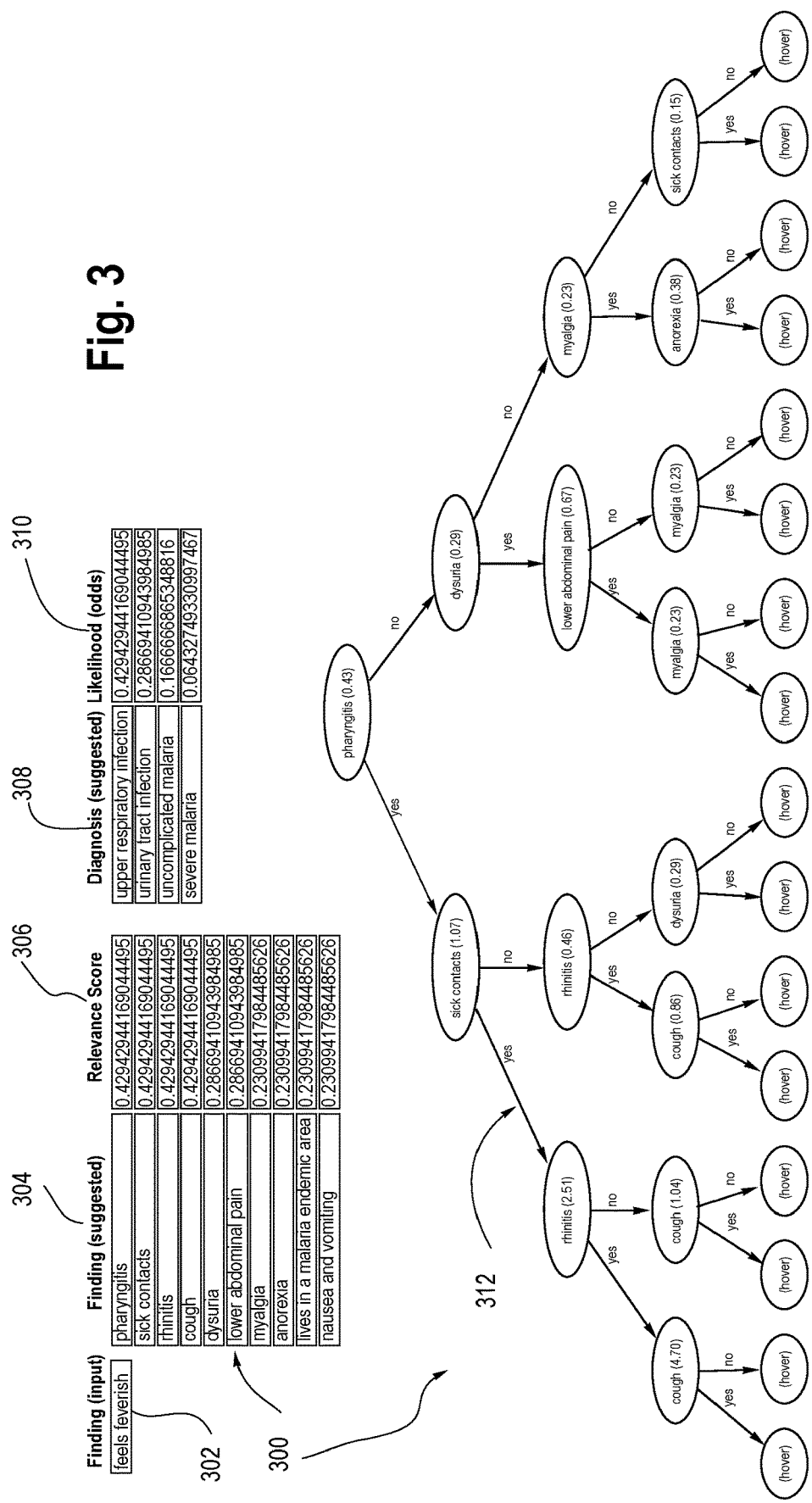
FIG. 3 is an illustration of a Diagnostics Model Explorer which provides visualizations of suggestions of additional findings or related tests produced by the inference engine of FIG. 1, indicia in the form of relevancy scores, and suggested diagnoses with probability scores.
Figure 4:
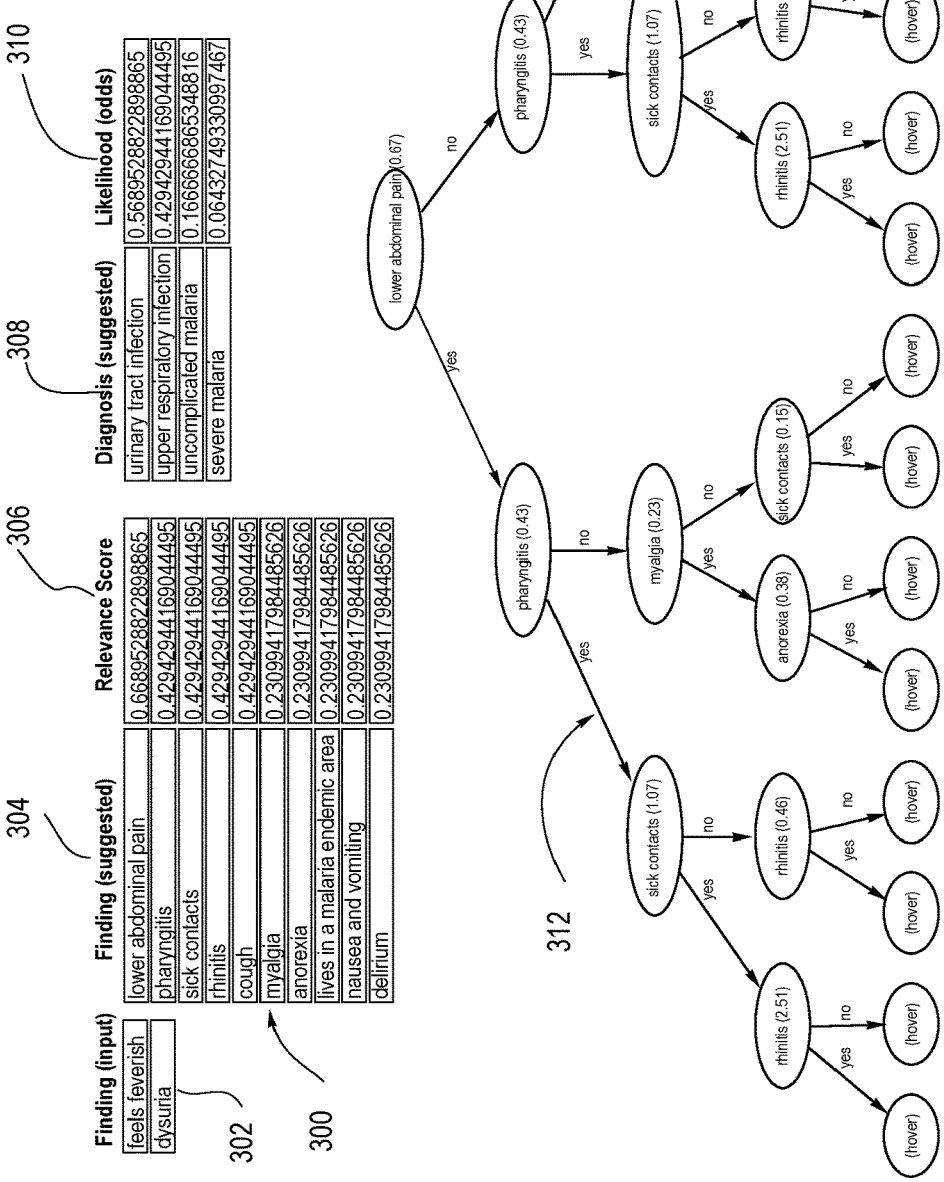
FIG. 4 is an illustration of the Diagnostic Model Explorer after the physician has selected an additional finding, showing a new ranking of suggested additional findings and a new ranking of suggested diagnoses.

FIG. 3 shows one example of how the interface 40 of the device 12 could display proposed diagnoses. In one embodiment, the device includes a tool or icon on the display of FIG. 1 which, when activated displays to the healthcare provider what we have termed a "Diagnostics Model Explorer." The Diagnostics Model Explorer visualizes the suggestions made by the inference engine, including proposed new findings and suggested diagnosis. The Diagnostics Model Explorer shows known findings in the leftmost column 302, suggestions for new findings in the second column 304, relevancy scores (i.e., "indicia") for the proposed new findings in the third column 306, and the differential diagnosis in the fourth column 308. The fifth column shows a likelihood score (odds) that the suggested diagnosis in column 308 is correct.

Below the textual and numerical data at the top of the display is a tree 312 showing a sequence of related findings or symptoms along with probability data linking the sequences to a diagnosis (the lowermost level of the tree). In this scenario, the most cost effective finding is pharyngitis, listed at the top of the tree. However, the physician is not required to obtain this finding to progress. For example, the physician can select "dysuria" (first branch, right), and it becomes a "known finding."

As indicated previously, when new findings are made, as in this case a new finding of "dysuria," the Diagnostic Model Explorer is updated. See FIG. 4. "Dysuria" is now listed in the first column 302 as a known new finding. The differential diagnosis is refreshed, putting urinary tract infection at the top of the column 308 of suggested diagnoses. The decision tree is also recalculated, placing "lower abdominal pain" as the best next finding to obtain as indicated at the top of column 304, since it has the highest relevancy score as indicated by the third column 306. Likewise, the diagnostic tree 312 is updated.

Figure 5:
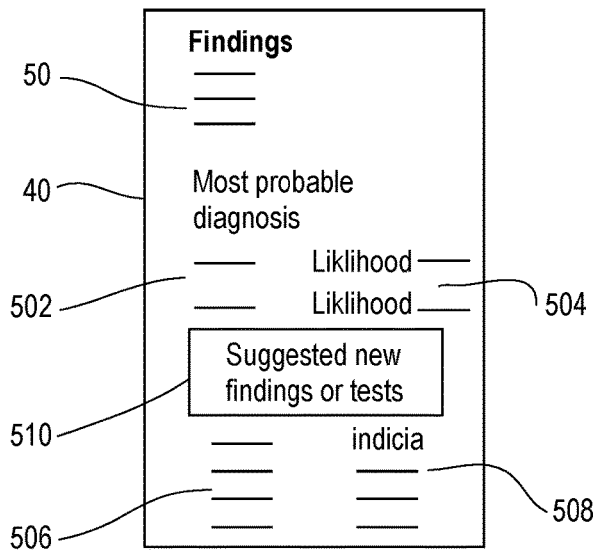
FIG. 5 is an illustration of a health-care provider facing interface of an electronic device showing a list of current known and pertinent findings for a patient, a list of most probable diseases and likelihood scores, and suggested new findings or tests with associated indicia.

FIG. 5 shows another arrangement of the display of the interface 40 of the electronic device in which the device includes in one screen a display of known findings 500, a display of most probable diagnosis 502, likelihood data for these diagnoses 504, and a display of suggested new findings or tests in one column 506 and associated indicia 508 for each of proposed additional tests or findings, such as for example relevancy scores, costs, or other attributes for the findings. In FIG. 5, the provider can click on the "suggested new findings or tests" icon 510 and the display of FIG. 6 appears. In this case there are two new tests which are suggested—a CT scan and an ultrasound. For each new test, the indicia include a "delta probability" and a cost. The delta probability reflects the degree of confidence in the accuracy of the diagnosis increases depending on the results of the particular test. Of course, the details of the design of the user interface of the device 12 is not particularly important and the examples of this disclosure are offered for purposes of illustration and not limitation.

Figure 6:
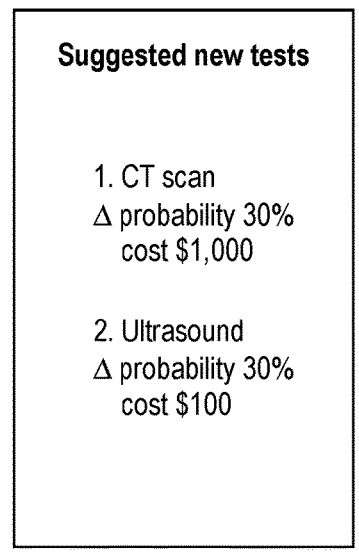
FIG. 6 shows the interface of FIG. 5 after the physician has selected one of the suggested new tests listed in FIG. 6; the display shows details of the suggested new tests and indicia in the form of delta probabilities and cost data.

Consider the following example: a patient may have a set of medical findings associated with a chief complaint, i.e., abdominal pain. From the medical findings, the inference engine 24, with the aid of the probabilistic model 16 and knowledge base, determine a set of the most probable diseases (appendicitis and gall bladder disease) and infers a set of two tests that differentiate the set of most probable diseases: 1) an abdominal CT scan and 2) an abdominal ultrasound. Indicia are also generated by the engine: based on the prevalences of the two diseases and the known medical findings the patient's probability of having gallbladder disease is 60% and appendicitis is 40%. This information is displayed in regions 502 and 504 of FIG. 5. A CT scan that shows an inflamed gall bladder would increase the probability of gallbladder disease being the correct diagnosis to 90%, and would decrease the probability of appendicitis to 10%, increasing the delta probability by 80%. An abdominal ultrasound that shows an inflamed gallbladder has the same delta probability. A cost comparison indicates that the CT scan is 10 times more expensive than the abdominal ultrasound, but both tests have the same delta probability, i.e., have the same diagnostic effectiveness in this particular situation. This information is displayed on the device 12 as shown in FIG. 6. Accordingly, the healthcare provider may then pursue the abdominal ultrasound, since it has the same medical effectiveness as a CT scan but costs much less.

Figure 7:
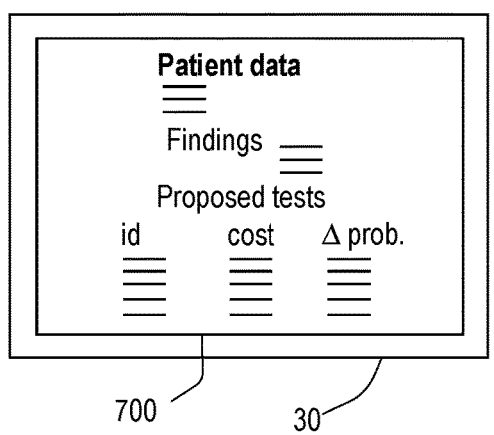
FIG. 7 shows an interface of a healthcare payer workstation showing a display of patient data, findings, and proposed tests including cost and delta probabilities to assist in making reimbursement decisions. A similar display could be provided on a web-based interface for a patient to assist them in making decisions.

FIG. 7 shows an example of the payer interface on the computer terminal 30 of FIG. 1. The payer interface includes patient data, findings and proposed tests (identification code, cost and delta probability). The payer viewing the cost and delta probability in this situation may not authorize a physician's order of the CT scan and instead authorizes the abdominal ultrasound since they both have the same effectiveness but the abdominal ultrasound has a cost of only 1/10 that of the CT scan.

Figure 8:
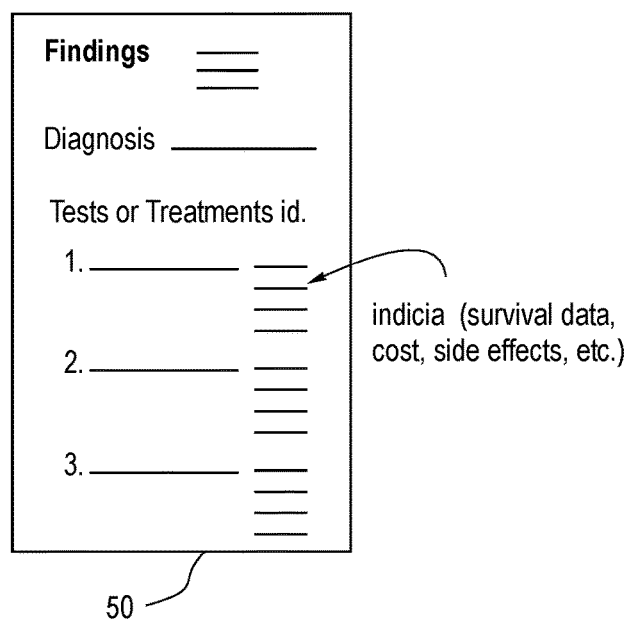
FIG. 8 shows the display on an electronic device showing known findings, a diagnosis, and proposed treatments for a patient along with indicia for each of the proposed treatments, including things such as survival data, cost data, side effects, etc. to assist a provider and patient in making treatment decisions; such information could also be displayed on workstation for a payer to assist in making reimbursement and coverage decisions.

FIG. 8 is an illustration of the web interface 50 for a patient. The patient logs into the medical records system for the hospital or provider they are using and navigate to a page having the interface 50, which includes a display of the pertinent aspects of their medical records, including findings, a diagnosis and proposed additional tests or treatments. Each of the proposed additional tests or treatments is associated with indicia, such as cost, delta probability, survivability data, relevancy, side effects, risks, etc., Inference Engine 24 and Validated Probabilistic Model 16

As indicated above, inference engine 24 makes suggestions of diagnosis and additional findings making use of a stored knowledge base 18 and validated probabilistic model 16. The data in the knowledge base 18 can be curated manually (e.g., from aggregated electronic medical records, medical literature, textbooks, expert user input, etc.) or gathered from the flow of information through the system as describe above. The system includes an interpreter 120 to augment the knowledge base using information extraction from medical texts, records, or user input.

The probabilistic model 14 uses two medical concepts: diagnoses and findings. These concepts have attributes, like severity, informer, and method, that are useful for ranking the concept's relevance. For example, a finding with a costly method can be ranked lower than one with a less costly method. The model API 22 (FIG. 1) supports queries like: "find all concepts with an effectiveness relationship to concept A", "find all attributes of concept B", etc., taking advantage of the format of the data indicated by the box 100 in FIG. 1, namely the linking of findings to attributes, linking of diagnoses to attributes, and providing effectiveness attributes (sensitivity, specificity) between findings, or sets of findings, and diagnoses.

Relationships exist between these concepts, such as between diagnoses, between findings, as indicated in the box 100 of FIG. 1. The diagnosis-finding relationship has two values, sensitivity (true positive rate) and specificity (true negative rate), modeled after diagnostic tests. From this, we can derive two synthetic relationships, one for a positive finding and one for a negative finding.

Original Relationship
  Diagnosis—finding: sensitivity, specificity
Becomes
  Diagnosis—pos. finding: LR+ or sensitivity/(1−specificity)
  Diagnosis—neg. finding: LR− or (1−sensitivity)/specificity
(where LR is Likelihood Ratio).

With this knowledge representation, we can guide the user towards a differential diagnosis. Unlike traditional decision-tree-based instruction, our method does not require any specific input order, simply the known set of findings. Eventually the "known findings" input can be expanded to include anything and everything we might know about the patient e.g., f(patient).

$$f(\text{known findings})=\text{potential diagnosis}$$

Diagnoses are ranked based on their posttest probability/odds given a set of known findings. The likelihood ratios can be derived from concept relationships and are consequently used to compute the posttest odds.

$$\text{posttest odds}=\text{likelihood ratio}*\text{pr-test odds}$$

This is derived from Bayes' theorem, which states:

$$p(D|F)=p(F|D)/p(F)*p(D)$$

Using Bayesian inference, we can update the diagnosis probability as we add findings; the posttest odds becomes the pretest odds of the next input. Thus, given a set of independent, equally prevalent findings F1 . . . Fx (i.e. p(F)=1), the posttest odds of a diagnosis D is: p(D|F1 . . . Fx)=p(F1|D)p(F2|D) . . . p(Fx|D)p(D).

$$g(\text{known findings})=\text{relevant findings}$$

Referring again to FIG. 1, the engine 24 works essentially as follows. The engine queries the model 16 and applies an algorithm in order to draw inferences from the model 16. For example, the engine, given a set of known findings for a patient, seeks to answer the question: "what tests should be performed next?" To answer the question, the engine could apply the following algorithm:
1. Query the model for disease concepts related to the known findings.
2. Score the disease concepts by computing the pre-test probability given the disease prevalence and known test results.
3. Query the model for related tests.
4. Score the tests based on factors like the post-test probability (effectiveness), cost, urgency, frequency/rarity and/or other factors. Data as to the results of the inference engine are then presented to the electronic device 12 of the healthcare provider, the interface 50 for the patient, and/or the payer computer terminal 30.

FIGS. 9-13 will illustrate further examples of how the model 16 and inference engine 24 work to generate diagnoses and findings/tests.

Figure 9:
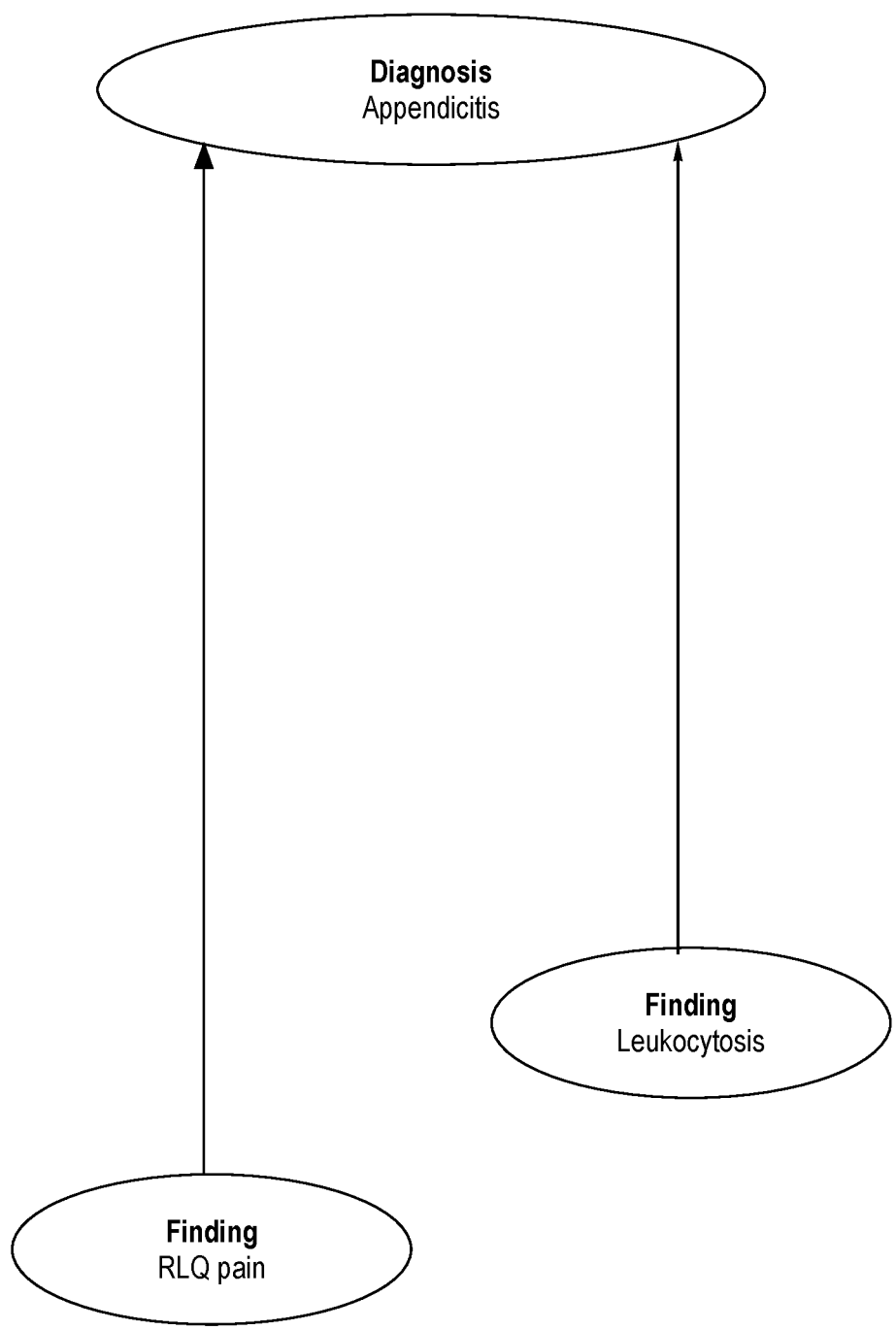
FIG. 9 is an illustration of an example of how the inference engine of FIG. 1 works.

In FIG. 9 is an example of how the decision-making engine 24 would work. The engine must infer the most cost-effective test between the top two diagnoses, appendicitis and diverticulitis. In this implementation, cost is weighed over effectiveness. The test for each finding is sorted by cost first, then by likelihood ratio. RLQ (Right Lower abdominal Quarter) can be determined by the interview, which is inexpensive as compared to a lab test required to determine leukocytosis. Therefore, the engine infers that RLQ pain is the best finding to obtain.

Figure 10:
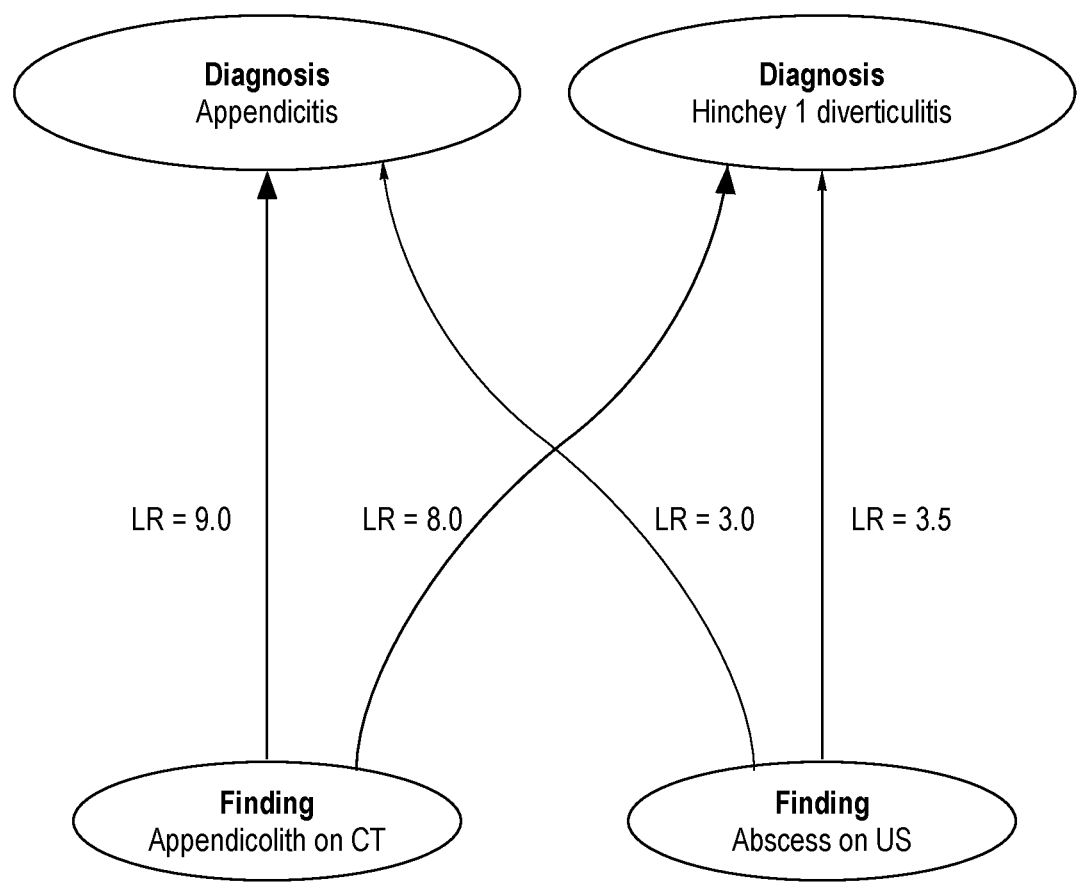
FIG. 10 is an illustration of an example of how the inference engine of FIG. 1 prioritizes findings that differentiates between two different diagnoses.

FIG. 10 illustrates that the engine 24 will prioritize findings that differentiate between diseases. For example, assume here that a CT scan and ultrasound (US) are equally costly. A CT scan that shows appendicolith strongly suggests appendicitis (LR 9.0) and strongly suggests against diverticulitis (LR −8.0). An abscess on ultrasound has an LR of 3.0 for appendicitis and 3.5 for diverticulitis, which does not differentiate between the diseases. Therefore the engine would recommend a CT scan over US.

Figure 11:
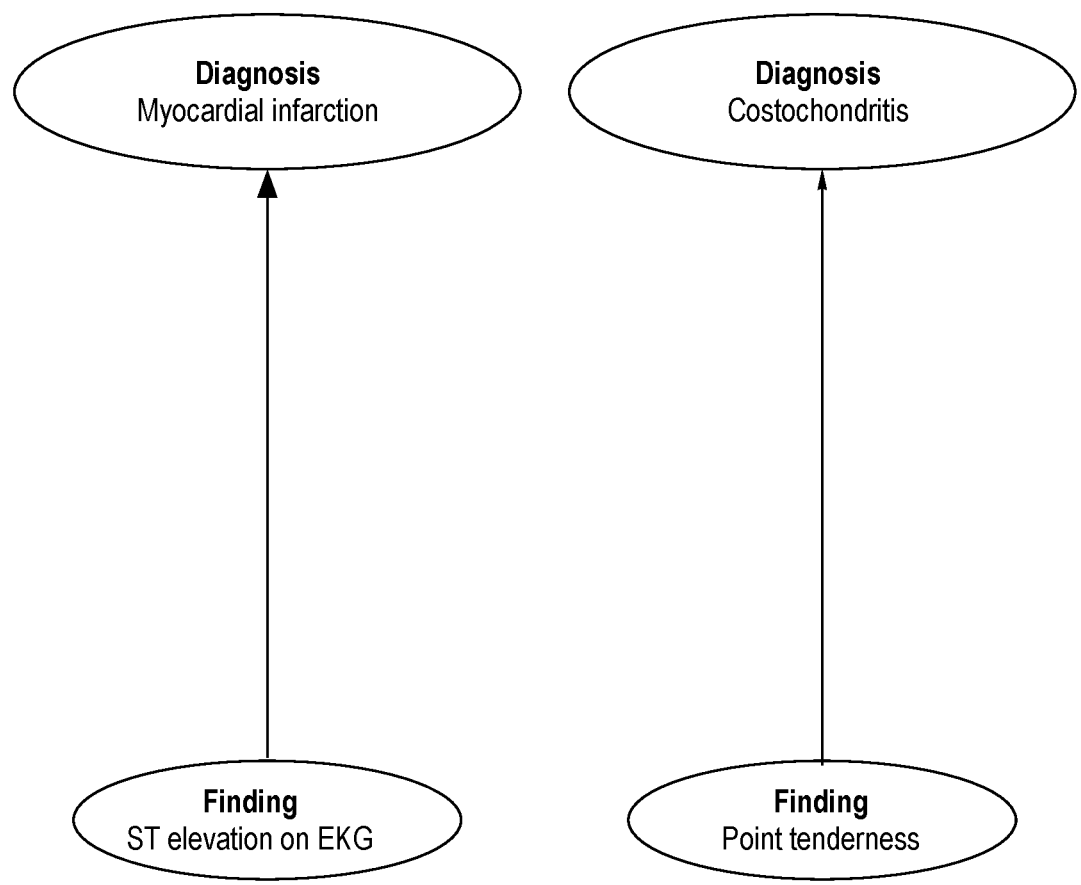
FIG. 11 is an illustration of how the inference engine accounts for disease severity and prioritizes findings that rule in or out severe and urgent diseases over findings for non-urgent diseases.

FIG. 11 illustrates that the engine 24 accounts for disease severity and prioritizes findings that rule in or out severe and urgent diseases over findings for non-urgent diseases. In this example, myocardial infarction is more threatening compared to costochondritis, therefore, the engine would recommend obtaining an EKG over palpating the sternum for point tenderness.

Figure 12:
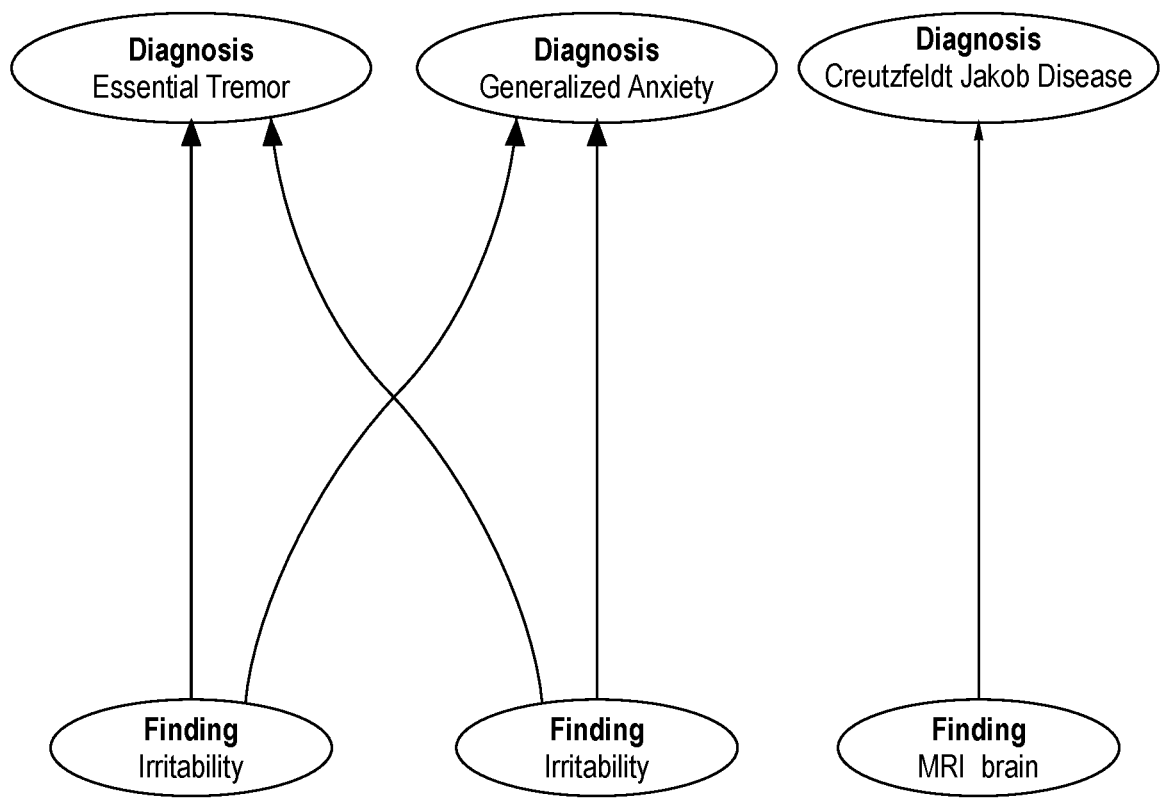
FIG. 12 an illustration of how the inference engine considers prevalence of diseases for ranking or scoring potential diagnoses; it seeks findings that differentiate more common diseases as compared to very rare diseases.

FIG. 12 illustrates that the engine 24 considers prevalence (from the validated probabilistic model 16) of the diseases in the differential. While it considers all diseases, it seeks findings that differentiate the more common diseases. For example, Creutzfeldt Jakob disease is extremely rare compared to generalized anxiety and essential tremor, and therefore would prioritize findings or tests that differentiate the more common diseases.

Figure 13:
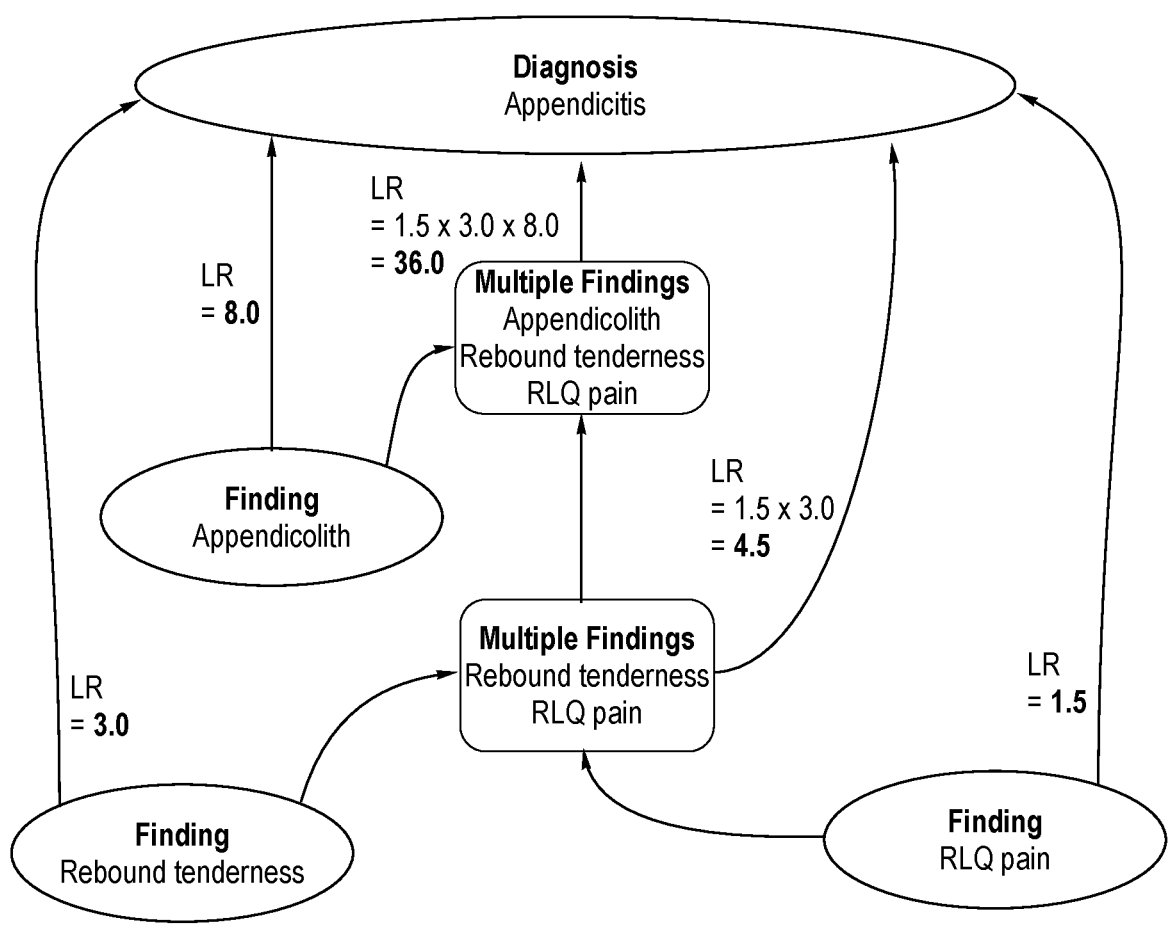
FIG. 13 is an illustration of how the inference engine determines a likelihood of disease from multiple findings.

FIG. 13 illustrates that as findings are collected, their individual LRs disease are multiplied for each disease. If RLQ pain is the only known finding, the likelihood ratio of appendicitis is the prevalence of appendicitis multiplied by 1.5. The additional finding of rebound tenderness will multiply 1.5 by 3.0. Similarly, an appendicolith will multiply 4.5 by 8.0. These three findings increase this patient's likelihood of having appendicitis 36 times greater than the general population.

While the illustrated embodiment illustrates a simple Bayesian approach for the probabilistic model, other types of models could be used which are known in the literature, for example the patent literature described in the Background section of this document.

In view of the above, a method has been disclosed for evaluating medical effectiveness of one or more diagnostic tests from a set of known findings as to a patient, comprising:
a) providing a computing device 12 (FIG. 1) containing a software application which is used by a healthcare provider to review the patient's medical history and enter findings as to the patient's condition or symptoms (see FIG. 2);

b) providing a validated probabilistic health model 16 informed from aggregated electronic medical records or other sources of medical knowledge; and c) using a computer processor 24 configured as a medical knowledge-based inference engine operating on the patient's medical history and findings and the validated probabilistic health model:
   (1) determining a set of the most probable diseases of the patient,
   (2) suggest a set of one or more tests or additional findings that differentiate the set of most probable diseases, and
   (3) generating indicia indicating effectiveness or relevancy of the set of one or more tests or additional findings. (See FIGS. 2-8)

Furthermore, the method can include the step of transmitting the indicia from the engine to an application residing on a healthcare payer network configured to facilitate reimbursement or authorization decisions regarding the one or more tests, as for example described above in the context of FIGS. 1 and 7.

The method may further include the step of transmitting the indicia from the engine 24 to the software application residing on the computing device 12 or 30.

In one embodiment, the computing device 12 further includes an interface (FIG. 2), and wherein the method further comprises the step of presenting on the interface information as to at least one of (i) the set of the most probable diseases of the patient and (ii) a set of one or more tests that differentiate the set of most probable diseases, (iii) the indicia indicating effectiveness of the one or more tests or (iv) visualizations of the suggestions made by the inference engine, see FIGS. 2-8 and the above description.

As explained above the method may further include a step of transmitting to a web-based patient interface 50 providing patients with medical effectiveness information data for generating a display of at least one of (i) the set of the most probable diseases of the patient and (ii) a set of one or more tests or additional findings that differentiate the set of most probable diseases, (iii) the indicia indicating effectiveness or relevancy of the one or more tests, or (iv) visualizations of the suggestions made by the inference engine, such as shown in FIG. 8.

In another aspect, we have described a system in the form of a) a validated probabilistic health model 14 including a database 18 of medical knowledge informed from aggregated electronic medical records or other sources of medical knowledge; and b) a medical knowledge-based inference engine 24 operating a patient's medical history and findings and the validated probabilistic health model to (1) determine a set of the most probable diseases of the patient, (2) suggest a set of one or more tests or additional findings that differentiate the set of most probable diseases, and (3) generate indicia indicating effectiveness or relevancy of the one or more tests or additional findings; and c) an interpreter 120 converting raw medical information from at least one of documents sources, medical records, payment data or expert input from healthcare providers into a format useful to the database of medical knowledge and supplying the information in the format to the database 18. The format in the illustrated embodiment is in the form of relationships between medical findings and diagnoses, effectiveness scores for the relationships, and attributes of the findings and the diagnoses. As an example the attributes of the findings could include a cost attribute. The attributes of the diagnoses could include a severity attribute, or a frequency attribute, or a treatment attribute or attributes.

In another aspect, a method has been described for assisting in making reimbursement or coverage decisions for medical care of a patient having a diagnosis and a medical history including findings. The method includes the steps of a) providing a validated probabilistic health model 14 including a database 18 of medical knowledge informed from aggregated electronic medical records or other sources of medical knowledge; b) providing a medical knowledge-based inference engine 24 operating on the patient's medical history and findings and the validated probabilistic health model to (1) determine a set of potential treatments for the patient and (2) generate indicia indicating effectiveness or relevancy of the potential treatments in the set; c) providing an interpreter 120 converting raw medical information from at least one of document sources, medical records, payment data or input from healthcare providers into a format useful to the database of medical knowledge and supplying the information in the format to the database; and d) generating data for a payer-facing interface (see FIG. 1, 30; FIG. 7) for presenting the set of potential treatments for the patient and the indicia to assist a user of the payer-facing interface in making a reimbursement or coverage decision.

We claim:

1. A system for evaluating diagnostic effectiveness of one or more diagnostic tests or additional findings from a set of known findings as to a patient, comprising:
   a) a computer system storing a validated probabilistic health model including a database of medical knowledge informed from aggregated electronic medical records or other sources of medical knowledge; and
   b) a processor and a memory having stored thereon instructions implementing a medical knowledge-based machine learning model operating on the patient's medical history and findings and the validated probabilistic health model, wherein the instructions, upon execution by the processor, cause the system to perform operations comprising: (1) providing, via an interactive graphical user interface, a set of known findings about a patient, wherein the set of known findings is generated by the machine learning model based on the patient's medical history, (2) determining a set of additional findings indicative of one or more most probable diseases of the patient, wherein the machine learning model generates one or more diagnosis-finding relationships between additional findings in the set of additional findings and associated diagnoses, (3) providing, via the interactive graphical user interface, the additional findings and associated relevance scores as nodes in an interactive relational tree, wherein the relational tree represents a related sequence of the one or more diagnosis-finding relationships between the additional findings and the associated diagnoses with respective likelihood scores, (4) receiving, via a selection of a node in the interactive relational tree of the interactive graphical user interface, a confirmation of a finding from the set of additional findings, (5) updating, based on the confirmation of the finding, the set of known findings by adding the finding to the set of known findings, (6) generating, using the machine learning model and based on the updated set of known findings, the set of additional findings with associated relevance scores, and the associated diagnoses with respective likelihood scores, and (7) displaying, via the interactive graphical user interface, an updated interactive relational tree.

2. The system of claim 1, further comprising an application residing on a healthcare payer network receiving the indicia from the machine learning model, the application configured to facilitate reimbursement or authorization decisions regarding the one or more diagnostic tests.

3. The system of claim 1, further comprising
a computing device containing a software application which is used by the healthcare provider to review the patient's medical history and enter findings as to the patient's condition or symptoms, wherein the computing device further includes an interface for presenting to the healthcare provider information as to at least one of (i) the one or more most probable diseases of the patient and (ii) a set of one or more tests or additional findings that differentiate one or more most probable diseases, (iii) the indicia indicating effectiveness or relevancy of the one or more tests, or (iv) visualizations of the suggestions made by the machine learning model.

4. The system of claim 1, further comprising a web-based patient interface providing patients with diagnostic effectiveness information, wherein interface provides a display of at least one of (i) the one or more most probable diseases of the patient and (ii) a set of one or more tests or additional findings that differentiate the one or more most probable diseases, (iii) the indicia indicating effectiveness or relevancy of the one or more tests, or (iv) visualizations of the suggestions made by the machine learning model.

5. The system of claim 1, wherein the operations further comprise storing raw medical information from at least one of document sources, medical records, payment data or input from healthcare providers in the database, wherein the database is configured to preserve one or more relationships between one or more of: a diagnosis, a diagnosis attribute, a finding, a finding attribute, a treatment, or a treatment attribute.

6. The system of claim 5, wherein the storing comprises storing effectiveness scores for the one or more relationships.

7. The system of claim 5, wherein the finding attribute includes a cost attribute, and wherein the diagnosis attribute includes a severity attribute.

8. The system of claim 1, wherein the operations further comprise:
receiving, via the interactive graphical user interface, a selection of a diagnostic test of the one or more diagnostic tests; and
updating, based on the selection, the indicia indicating diagnostic effectiveness or relevancy of the one or more diagnostic tests.

9. The system of claim 1, wherein the operations further comprise:
updating, based on a confirmation or a denial of a finding, one or more of the set of known findings, the set of additional findings, or the one or more diagnosis-finding relationships.

10. The system of claim 1, wherein the one or more diagnosis-finding relationships is based on a positive likelihood ratio and a negative likelihood ratio, wherein each likelihood ratio is based on (i) a sensitivity indicative of a true positive rate of a diagnosis, and (ii) a specificity indicative of a true negative rate for the diagnosis, and the operations further comprising:
determining the positive likelihood ratio as a ratio of the sensitivity and a relative specificity, wherein the relative specificity is a difference of the specificity from 1, and
determining a negative likelihood ratio as a ratio of a relative sensitivity and the specificity, wherein the relative sensitivity is a difference of the sensitivity from 1.

11. The system of claim 1, the operations further comprising:
ranking the one or more diagnostic tests based on respective costs and respective likelihood ratios.

12. The system of claim 1, the operations further comprising:
receiving, via the interactive relational tree of the interactive graphical user interface, a denial of a second finding from the set of additional findings,
wherein the updating of the set of additional findings comprises removing, based on the denial of the second finding, the second finding from the set of additional findings, and
wherein the generating of the updated set of additional findings and the associated diagnoses is performed based on the removing of the second finding from the set of additional findings.

13. The system of claim 1, wherein the providing of the set of known findings further comprises:
providing, by a diagnostics model explorer and via the interactive graphical user interface, the set of known findings about the patient, wherein the diagnostics model explorer is a tabular representation of the set of known findings, the set of additional findings with associated relevance scores, and the associated diagnoses with associated likelihood ratios.

14. A computer implemented method for evaluating diagnostic effectiveness of one or more diagnostic tests from a set of known findings as to a patient, comprising:
a) providing a validated probabilistic health model informed from aggregated electronic medical records or other sources of medical knowledge; and
b) using a computer processor and a memory having stored thereon instructions implementing a medical knowledge-based machine learning model operating on the patient's medical history and findings and the validated probabilistic health model, wherein the instructions, upon execution by the processor, cause the processor to perform operations comprising:
(1) providing, to a computing device which is used by a healthcare provider, a set of known findings about a patient, wherein the set of known findings are generated by the machine learning model based on the patient's medical history,
(2) determining a set of additional findings indicative of one or more most probable diseases of the patient, wherein the machine learning model generates one or more diagnosis-finding relationships between additional findings in the set of additional findings and associated diagnoses,
(3) providing, to the computing device, the additional findings and associated relevance scores as nodes in an interactive relational tree, wherein the relational tree represents a related sequence of the one or more diagnosis-finding relationships between the additional findings and the associated diagnoses with respective likelihood scores,
(4) receiving, from the computing device and via a selection of a node in the interactive relational tree of, a confirmation of a finding from the set of additional findings, (5) updating, based on the confirmation of the finding, the set of known findings by adding the finding to the set of known findings, (6) generating, using the machine learning model and based on the updated set of known findings, the set of additional findings with associated relevance scores, and the associated diagnoses with respective likelihood scores, and (7) displaying, via the interactive graphical user interface, an updated interactive relational tree.

15. The method of claim 14, further comprising the step of transmitting the indicia from the engine to an application residing on a healthcare payer network configured to facilitate reimbursement or authorization decisions regarding the one or more tests.

16. The method of claim 14, wherein the computing device further includes an interface, and wherein the method further comprises the step of presenting on the interface information as to at least one of (i) the one or more most probable diseases of the patient and (ii) a set of one or more tests that differentiate the one or more most probable diseases, (iii) the indicia indicating diagnostic effectiveness of the one or more tests or (iv) visualizations of the suggestions made by the machine learning model.

17. The method of claim 14, wherein the method further comprises the step of transmitting to a web-based patient interface providing patients with diagnostic effectiveness information data for generating a display of at least one of (i) the one or more most probable diseases of the patient and (ii) a set of one or more tests or additional findings that differentiate the one or more most probable diseases, (iii) the indicia indicating effectiveness or relevancy of the one or more tests, or (iv) visualizations of the suggestions made by the machine learning model.

18. A system for evaluating diagnostic effectiveness of one or more diagnostic tests or additional findings from a set of known findings as to a patient, comprising:
   a) a validated probabilistic health model including a database of medical knowledge informed from aggregated electronic medical records or other sources of medical knowledge;
   b) a medical knowledge-based machine learning model operating on a patient's medical history and findings and the validated probabilistic health model; and
   c) one or more processors, and a memory having stored thereon instructions that, upon execution by the one or more processors, cause the one or more processors to (1) determine a set of known findings about a patient, wherein the set of known findings is generated by the machine learning model based on the patient's medical history, (2) determine a set of additional findings indicative of one or more most probable diseases of the patient, wherein the machine learning model generates one or more diagnosis-finding relationships between additional findings in the set of additional findings and associated diagnoses, (3) provide the set of additional findings and associated relevance scores as nodes in an interactive relational tree, wherein the relational tree represents a related sequence of the one or more diagnosis-finding relationships between the additional findings and the associated diagnoses with respective likelihood scores, (4) receive, via a selection of a node in the interactive relational tree, a confirmation of a finding from the set of additional findings, (5) updating, based on the confirmation of the finding, the set of known findings by adding the finding to set of known findings, (6) generating, using the machine learning model and based on the updated set of known findings, the set of additional findings with associated relevance scores, and the associated diagnoses with respective likelihood scores, and (7) displaying, via the interactive graphical user interface, an updated interactive relational tree; and
   c) a computing device configured to store raw medical information from at least one of document sources, medical records, payment data or input from experts in the database, wherein the database is configured to preserve one or more relationships between one or more of: a diagnosis, a diagnosis attribute, a finding, a finding attribute, a treatment, or a treatment attribute.

19. The system of claim 18, wherein the storing comprises storing effectiveness scores for the one or more relationships.

20. The system of claim 18, wherein the finding attribute includes a cost attribute, and wherein the attributes diagnosis attribute includes a severity attribute.

21. A method for assisting in making reimbursement decisions for medical care of a patient having a diagnosis, and a medical history including findings, comprising the steps of:
   a) providing a validated probabilistic health model including a database of medical knowledge informed from aggregated electronic medical records or other sources of medical knowledge;
   b) providing a medical knowledge-based machine learning model operating on the patient's medical history and findings and the validated probabilistic health model to (1) determine a set of additional findings indicative of one or more most probable diseases of the patient, wherein the machine learning model generates one or more diagnosis-finding relationships between additional findings in the set of additional findings and associated diagnoses, (2) provide the set of additional findings and associated relevance scores as nodes in an interactive relational tree, wherein the relational tree represents a related sequence of the one or more diagnosis-finding relationships between the additional findings and the associated diagnoses with respective likelihood scores, (3) receive, via a selection of a node in the interactive relational tree, a confirmation of a finding from the set of additional findings, (4) update, based on the confirmation of the finding, the set of known findings by adding the finding to set of known findings, (5) generate, using the machine learning model and based on the updated set of known findings, the set of additional findings with associated relevance scores, and the associated diagnoses with respective likelihood scores, and (6) display an updated interactive relational tree;
   c) providing a computing resource for storing raw medical information from at least one of document sources, medical records, payment data or input from experts in the database, wherein the database is configured to preserve one or more relationships between one or more of: a diagnosis, a diagnosis attribute, a finding, a finding attribute, a treatment, or a treatment attribute; and
   d) generating data for a payer-facing interface for presenting the set of one or more additional findings or diagnostic tests and the indicia to assist a user of the payer-facing interface in making a reimbursement decision.

22. The method of claim 21, wherein the indicia comprise at least one of delta probabilities, likelihood ratios, or costs associated with the set of one or more additional findings or diagnostic tests.

23. The method of claim 21, wherein the storing comprises storing effectiveness scores for the one or more relationships.

24. The method of claim 23, wherein the finding attribute includes a cost attribute, and wherein the diagnosis attribute includes a severity attribute.

* * * * *